United States Patent [19]

Pigneul et al.

[11] Patent Number: 4,994,054
[45] Date of Patent: Feb. 19, 1991

[54] SELF-ATTACHING FASTENER PART NOTABLY FOR ALL-IN-ONE DISPOSABLE DIAPER AND PROCESS FOR MANUFACTURING IT

[75] Inventors: Raymond Pigneul, Durrenentzen; Rémy Ruppel, Horbourg; Jean Brellmann, Colmar, all of France

[73] Assignee: Kaysersberg, SA, Kayersberg, France

[21] Appl. No.: 279,152
[22] PCT Filed: Feb. 8, 1988
[86] PCT No.: PCT/FR88/00065
§ 371 Date: Oct. 7, 1988
§ 102(e) Date: Oct. 7, 1988
[87] PCT Pub. No.: WO88/06014
PCT Pub. Date: Aug. 25, 1988

[30] Foreign Application Priority Data

Feb. 10, 1987 [FR] France .................. 87 01590

[51] Int. Cl.$^5$ ............................................ A61F 13/16
[52] U.S. Cl. ........................... 604/391; 128/DIG. 15; 428/100; 24/306
[58] Field of Search ........ 604/366, 389, 386, 390–391; 428/100; 128/DIG. 15; 24/306

[56] References Cited

U.S. PATENT DOCUMENTS 4,299,223 11/1981 Cronkrite ..................... 604/390
4,537,591 8/1985 Coates ......................... 604/391

FOREIGN PATENT DOCUMENTS 8503625 8/1985 PCT Int'l Appl. .
1400080 7/1975 United Kingdom .
1438721 6/1976 United Kingdom .

Primary Examiner—C. Fred Rosenbaum
Assistant Examiner—Corrine Maglione
Attorney, Agent, or Firm—A. W. Breiner

[57] ABSTRACT

The invention relates to a self-attaching fastener of the buckles and grips type supplied notably as fastening means (2,3) in disposable articles (1). It relates in particular to a buckles part (3), of open structure fabric.

In order to be able to fix by means of a cold adhesive glue this part to a support such as a sheet of plastic material constituting the external face of a complete diaper, the invention proposes to associate the element to a film of synthetic resin on at least part of its surface not provided with buckles.

In a particular mode of embodiment, the film acts as linking layer for an additional layer consolidating the part.

13 Claims, 1 Drawing Sheet

SELF-ATTACHING FASTENER PART NOTABLY FOR ALL-IN-ONE DISPOSABLE DIAPER AND PROCESS FOR MANUFACTURING IT

The invention relates to disposable articles, particularly all-in-one diapers for babies or incontinent adults and involves a self-attaching fastening means of the buckles and grips type. It concerns in particular the part provided with buckles.

Patent application FR 86 12403 registered by the applicant describes an all-in-one diaper the fastening means of which, enabling the diaper to be fitted around the waist, are of the buckles and grips type. One of the part of each lateral fastener is mounted on a tab integral with one edge of the absorbent pad, on the rear part of the diaper, and the complementary part is fixed to the external face of the pad at the front part. In this way, after placing the diaper around the bottom, one can tighten it around the waist of the user by joining each of the lateral tabs to its complementary part.

In this patent application, the grips part is preferably mounted on the lateral tab and the buckles part on the external face of the pad.

In order to cut manufacturing costs of disposable articles, as far as possible, one attempts to use parts that are themselves intended to be discarded following use.

There exists on the market self-attaching fasteners the buckle part of which is constituted by a fabric provided on one of its faces with raised buckles enabling the grips to be attached and embodied in accordance with a loose reinforcement offering an open structure.

When it is wished to secure a part of this type, i.e. the buckles part, to the outer face of the pad, which is conventionally a polyethylene sheet, a hot-melt glue is generally used, which is adhesive at ambient temperature, between the part and the plastic sheet. In a production machine with a high output rate, the adhesive is applied to either of the faces before coming into contact, after which the part is laid on the sheet and pressing it to ensure the bond.

This linking mode commonly used in the domain considered is however not possible with the part of the type desired, owing to the fluidity of the adhesive substance. It passes through the open structure of the fabric when pressed and links together the buckles with which it is provided on the opposite face. These buckles, once glued flat, are not longer effective and it is no longer possible to attach the grips of the complementary self-attaching part. The fastener is unusable.

The object of the invention is a part for a self-attaching fastener made from a buckles part with an open structure fabric, enabling it in particular to be fixed to a support by means of a cold adhesive glue and is characterized in that the buckles part is covered at least in part by film of synthetic resin intended to form a screen between the fabric of the buckles part and the cold adhesive glue.

The expression "open structure" is defined as being a structure in which the opening between the meshes is sufficient to enable a fluid to pass, of viscosity corresponding to that of a hot-melt glue, when pressure is exerted on the part, under the conditions prescribed on the machines used in the domain of disposable articles.

In practice, it is recognized that a structure is open when, after the non-buckled face of the part has been coated with adhesive and the part is applied to a flat support, the buckles can be glued together by pressing moderately with the finger on the buckled surface.

The skin is preferably obtained by coating a glue deposited hot, the viscosity of which is sufficient to prevent it passing through the meshes of the fabric and which, once cold, has no further residual tack. It is reminded that "tack" is the ability of an adhesive to form immediately a joint of measurable strength.

This arrangement offers many advantages:

After cooling, the skin forms a screen. During pressing, the cold adhesive bond is maintained between the skin and the sheet of polyethylene and links them without passing through the fabric. The efficiency of the buckles is not impaired.

Implementation is very simple, since it suffices in the case of an adhesive resin without cold tack to carry out an initial gluing operation with this resin, to cool the skin formed and thereafter to apply the part by means of the cold adhesive glue.

Depending on its constituent material and thickness, the glue stiffens the fabric and improves its behaviour. This property makes it easier for the product to pass through the machine.

According to another aspect of the invention, the rigidity and strength of the part is improved yet further by adding to it an additional support through the synthetic resin skin.

This support may be a film of plastic material such as polyethylene, a woven tissue, a non-woven tissue, a synthetic grid or even a paper.

The invention is developed in greater detail in the non-limitative description which follows two modes of embodiment, with relation to the drawings appended where:

Figure 1:
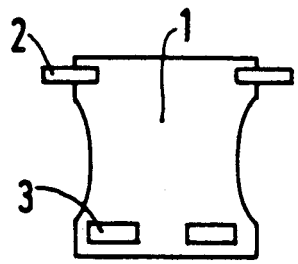
FIG. 1 shows an all-in-one diaper fitted with self-attaching fasteners.

FIG. 1 shows a complete all-in-one diaper 1, fitted with self-attaching fasteners. The view is of the front face of the diaper. On its lateral pads 2 are mounted grips type self-attaching parts in accordance with the information of patent application FR 86 02403 of the applicant. However, these grip parts can clearly be of any type. At the other end of the diaper the buckle parts 3 are provided, complementary to the self-attaching fastener. These parts are glued directly to the external face of the diaper which is conventionally embodied with a polyethylene sheet. However, the invention can also be applied to articles the external face of which is in any fabric, for instance non-woven.

When a buckle part is used the fabric of which has tightened meshes, one can without difficulty provide the linkage by means of a viscous layer of cold adhesive glue inserted between the external sheet of the diaper and the part.

Figure 2:
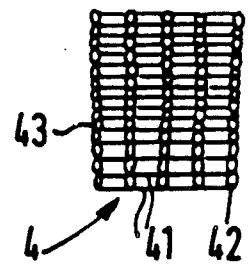
FIG. 2 shows a buckles fabric of open structure.

However, when one wishes to use an open structure part 4 as shown schematically in FIG. 2, the glue passes through the fabric during the pressing stage. A part of this type is sold by Société LOUISON under the reference 4090. This part is a teased knitted mesh known as disposable, the warp thread of which is in 40 Drs polyamide and comprises 16 columns and 16 rows per $cm^2$, with a fabric weight of about 90 g/m2. FIG. 2 shows the columns 41, the buckles 42 and the rows 43. For such a disposable teased mesh, with this caliber thread, the density of the rows and columns per $cm^2$ can vary from 8 to 24.

The gap between the columns on the one hand and the meshes on the other is sufficiently wide to enable a fluid to pass, even a viscous fluid such as a cold adhesive glue, for example the glue sold by Société BELIX under the reference 72120, or the glue sold by Société NATIONAL under the reference DUROTACK 108.

Figure 3:
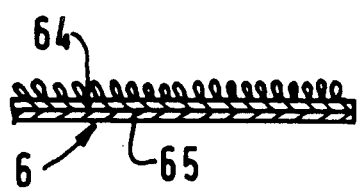
FIG. 3 is a cross-sectional view of the fastener part according to the invention.

To remedy this drawback, in accordance with the invention FIG. 3, a part 6 is used consisting of the buckles part 64 of the above type, to which a film 65 of a synthetic resin is applied. This film can cover the entire surface or alternatively by distributed in parallel strips or intermittent portions. A glue sold by Société BELIX under the reference FERUWELD 204 has been used that can be deposited by means of a nozzle or disk applicator. The fusion temperature of this mixture if 94° C. and its blockage point 50° C.; accordingly, at ambient temperature, there is no longer tack. Another glue that is suitable is the glue sold by Société FULLER under the reference UNATACK 50. This film 65 forms a screen between the fabric and the adhesive to which the part is to be fixed to the sheet of polyethylene of the diaper.

Figure 4:
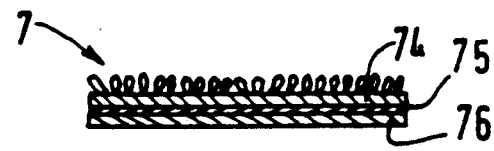
FIG. 4 is a cross-sectional view of a second form of the fastener part according to the invention.

According to another form of embodiment of the invention, to form the buckles part 7, and as shown in FIG. 4, an additional layer 76 is arranged, providing a support, on the resin film 75, thus providing the linkage between the layer 76 and the buckles part 74. The layer 76 must be in material that is both flexible and strong and may be a paper, a woven textile, a plastic film, a non-woven fabric, or a synthetic grid for example that sold under the trade name SCRINYL by the applicant and described in patent FR 73 29362. This additional layer not only provides strength but also a certain rigidity to the complex thus obtained, facilitating its use in a machine.

Figure 5:
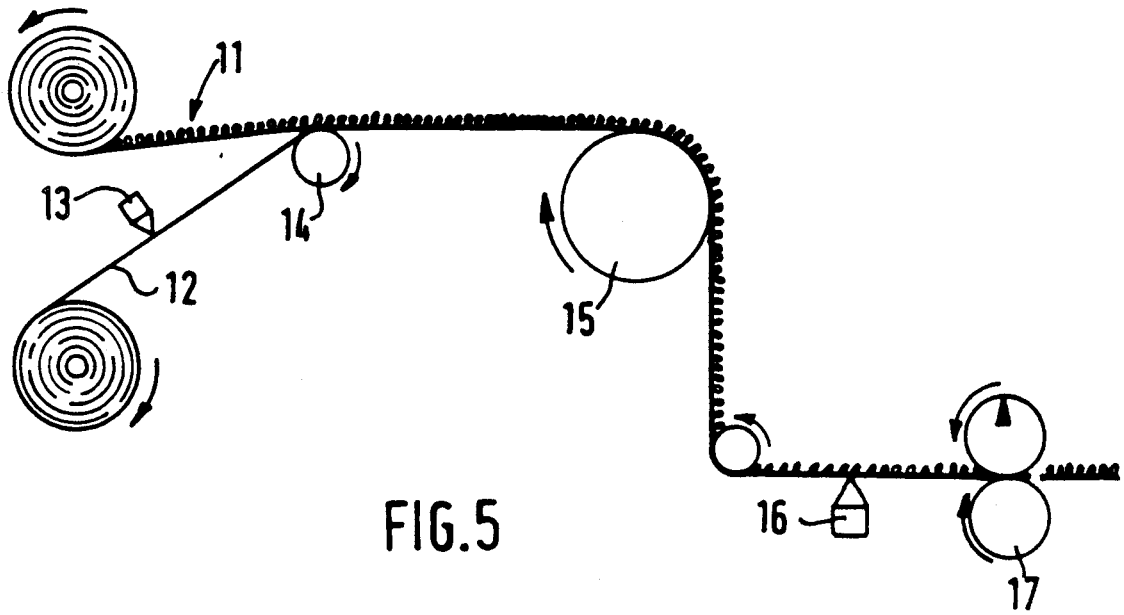
FIG. 5 is a diagram of a device enabling the part represented in FIG. 4 to be embodied.

FIG. 5 schematically shows a device enabling elements shown in FIG. 4 to be embodied. A strip of buckles fabric 11 is unwound from a reel mounted to rotate around an axis. In the same fashion, a strip 12 of material, that is to constitute the support layer of part 7, is unwound from a reel mounted on an axis. The two strips 11 and 12 join together on a roller 14. Strip 12 is coated between the reel and the roller 14 with a thin film of hot-melt glue without cold tack, such as the FERUWELD 204 glue, by means of a nozzle 13. The complex formed is then laid around a drum 15 which can be cooled by water circulation, so as to lower the temperature of the adhesive until it no longer has tack. Downstream from the drum, by means of a nozzle 16, a cold adhesive hot-melt glue is applied to strip 12 and the complex is cut by means of knives 17 into parts 7 ready for use, which can be taken up by appropriate means not shown to be deposited on the sheet forming the external face of the diaper.

It is also possible to wind the complex in a reel after cooling it for temporary storage so that it can be used later.

What is claimed is:

1. A disposable diaper comprising an external surface, an internal surface and a fastening system having a buckles part and a grip part positioned on said diaper in such a manner that when said buckles part and said grip part are interlocked, said interlocked buckles part and grip part are capable of holding said diaper in position on a user of said diaper, wherein at least said buckles part of said fastening system is affixed to said external surface of said diaper and comprises a support material having an open mesh structure and a plurality of raised buckles on a first side of said support material, a cold melt adhesive applied to a second side of said support material to affix said support material to said external surface of said diaper, and an adhesive having no tack at ambient temperature positioned on said second side of said support material between said support material and said cold melt adhesive to provide a screen between said support material and said cold melt adhesive.

2. A disposable diaper according to claim 1 wherein said adhesive having no tack at ambient temperature only covers a portion of said second side of said support material.

3. A disposable diaper according to claim 2 wherein said adhesive having no tack at ambient temperature is present in a plurality of parallel strips on said support material.

4. A disposable diaper according to claim 1 wherein said buckles part further comprises a second support material positioned between said adhesive having no tack at ambient temperature and said cold melt adhesive.

5. A disposable diaper according to claim 4 wherein said second support material is either paper, a non-woven fabric, a woven fabric, a material having a grid-like structure or a plastic film.

6. A disposable diaper according to claim 1 wherein said adhesive having no tack at ambient temperature is a hot melt adhesive.

7. A method of making a buckles part for a fastening system, said fastening system comprising a buckles part and a grip part wherein said buckles part is attached to an external surface of s disposable diaper and said grip part is attached to said disposable diaper in such a manner that when said buckles part is interlocked with said grip part, said buckles part and said grip part serve to hold said diaper on a user of said diaper, said method comprising unwinding a support material having an open mesh structure which is present as a continuous strip of material and has a plurality of raised buckles upstanding from a first side of said support material, applying an adhesive which has no tack at ambient temperature to a second side of said support material, applying a cold melt adhesive to said adhesive having no tack at ambient temperature on said support material, cooling the combined material formed, and cutting said strip of said support material at predetermined intervals.

8. A method according to claim 7 wherein said adhesive having no tack at ambient temperature is applied as a plurality of continuous parallel strips to said second side of said support material.

9. A method according to claim 7 wherein said adhesive having no tack at ambient temperature is a hot melt adhesive.

10. A method of making a buckles part for a fastening system, said fastening system comprising a buckles part and a grip part wherein said buckles part is attached to an external surface of a disposable diaper and said grip part is attached to said disposable diaper in such a manner that when said buckles part is interlocked with said grip pat, said buckles part and said grip part serve to hold said diaper on a user of said diaper, said method comprising unwinding a first support material which is present as a continuous strip, applying an adhesive which has no tack at ambient temperature to a first side of said first support material, unwinding a second support material having an open mesh structure which is present as a continuous strip and has a plurality of raised buckles upstanding from a first side of said second support material, pressing said adhesive-containing first side of said first support material to a second side of said second support material, applying a cold melt adhesive to a second side of said first support material, cooling the combined material formed, and cutting the strips of said first and said second support materials at predetermined intervals.

11. A method according to claim 10 wherein said first support material is either paper, a non-woven fabric, a woven fabric, a material having a grid-like structure or a plastic film.

12. A method according to claim 10 wherein said adhesive having no tack at ambient temperature is applied as a plurality of continuous parallel strips to said first side of said first support material.

13. A method according to claim 10 wherein said adhesive having no tack at ambient temperature is a hot melt adhesive.

* * * * *